(12) United States Patent
Tuerler et al.

(10) Patent No.: US 10,357,578 B2
(45) Date of Patent: Jul. 23, 2019

(54) PRODUCTION OF 43SC RADIONUCLIDE AND RADIOPHARMACEUTICALS THEREOF FOR USE IN POSITRON EMISSION TOMOGRAPHY

(71) Applicant: PAUL SCHERRER INSTITUT, Villigen PSI (CH)

(72) Inventors: Andreas Tuerler, Ostermundigen (CH); Nicholas Van Der Meulen, Schinznach Dorf (CH); Maruta Bunka, Remigen (CH)

(73) Assignee: Paul Scherrer Institut, Villigen PSI (CH)

( * ) Notice: Subject to any disclaimer, the term of this patent is extended or adjusted under 35 U.S.C. 154(b) by 0 days.

(21) Appl. No.: 15/310,864

(22) PCT Filed: May 7, 2015

(86) PCT No.: PCT/EP2015/060014
§ 371 (c)(1),
(2) Date: Nov. 14, 2016

(87) PCT Pub. No.: WO2015/173098
PCT Pub. Date: Nov. 19, 2015

(65) Prior Publication Data
US 2017/0087260 A1  Mar. 30, 2017

(30) Foreign Application Priority Data
May 13, 2014 (EP) ..................... 14168136

(51) Int. Cl.
| | | |
|---|---|---|
| A61K 51/00 | (2006.01) | |
| C01F 17/00 | (2006.01) | |
| C07F 5/00 | (2006.01) | |
| G21G 1/00 | (2006.01) | |
| A61K 51/08 | (2006.01) | |
| G21G 1/10 | (2006.01) | |

(52) U.S. Cl.
CPC ............ *A61K 51/088* (2013.01); *C01F 17/00* (2013.01); *C01F 17/0006* (2013.01); *C07F 5/00* (2013.01); *G21G 1/001* (2013.01); *G21G 1/10* (2013.01); *G21G 2001/0094* (2013.01)

(58) Field of Classification Search
CPC ............ A61K 51/00; C01F 17/00; G21G 1/00
See application file for complete search history.

(56) References Cited

U.S. PATENT DOCUMENTS

| | | | |
|---|---|---|---|
| 5,126,272 A | 6/1992 | Kingston, Jr. et al. | |
| 6,011,825 A * | 1/2000 | Welch ................. | G21G 1/10 376/195 |
| 6,352,682 B2 | 3/2002 | Leavitt et al. | |
| 6,530,988 B1 | 3/2003 | Silenius | |
| 7,335,748 B2 | 2/2008 | Harkins et al. | |
| 8,926,943 B2 | 1/2015 | Karlson et al. | |
| 9,056,142 B2 | 6/2015 | Karlson et al. | |
| 2002/0077306 A1 | 6/2002 | Dinkelborg et al. | |
| 2005/0019845 A1 | 1/2005 | Harkins et al. | |
| 2011/0305618 A1 | 12/2011 | Graham et al. | |

FOREIGN PATENT DOCUMENTS

| | | |
|---|---|---|
| CA | 2194558 A1 | 2/1996 |
| CN | 1055767 A | 10/1991 |
| CN | 1213316 A | 4/1999 |
| CN | 1496411 A | 5/2004 |
| CN | 102292461 A | 12/2011 |
| CN | 103760279 A | 4/2014 |
| JP | H03191860 A | 8/1991 |
| JP | 2000026118 A | 1/2000 |
| JP | 2007527403 A | 9/2007 |

(Continued)

OTHER PUBLICATIONS

H.S. Plendl et al. Low-Lying energy levels in odd-mass Sc isotopes, Nuclear Physics 73, 131-144. (Year: 1965).*
W.R. McMurray et al., A Study of the Ca(p,n)Sc reactions, Nuclear Physics, A99, 6-16 (Year: 1967).*
Cristina Muller et al. Promises of Cyclotron-Produced 445c as a Diagnostic Match for Trivalent b2-Emitters: In Vitro and In Vivo Study of a 44Sc-DOTA-Folate Conjugate, J. Nucl. Med, 54, 2168-2174. (Year: 2013).*
Seweryn Krajewski et al., Simple Procedure of Dotatate Labelling With Cyclotron Produced 44SC and 43SC Nucl. Med Rev. 15 Suppl A22-27 (Year: 2012).*
T.B. Grandy et al., The 42Ca(d,n)43Sc Reaction at Ed=5.15 MeV, Nuclear Physics A111 469-480. (Year: 1968).*

(Continued)

*Primary Examiner* — Michael G. Hartley
*Assistant Examiner* — Jagadishwar R Samala
(74) *Attorney, Agent, or Firm* — Laurence Greenberg; Werner Stemer; Ralph Locher

(57) ABSTRACT

The radionuclide $^{43}$Sc is produced at commercially significant yields and at specific activities and radionuclidic purities which are suitable for use in radiodiagnostic agents including imaging agents. In a method, a solid target having an isotopically enriched target layer prepared on an inert substrate is positioned in a specially configured target holder and irradiated with a charged-particle beam of protons or deuterons. The beam is generated using an accelerator such as a biomedical cyclotron at energies ranging from 3 to about 22 MeV. The method includes the use of three different nuclear reactions: a) irradiation of enriched $^{43}$Ca targets with protons to generate the radionuclide $^{43}$Sc in the nuclear reaction $^{43}$Ca (p,n)$^{43}$Sc, b) irradiation of enriched $^{42}$Ca targets with deuterons to generate the radionuclide $^{43}$Sc in the nuclear reaction $^{42}$Ca(d,n)$^{43}$Sc, and c) irradiation of enriched $^{46}$Ti targets with protons to generate the radionuclide $^{43}$Sc in the nuclear reaction $^{46}$Ti (p,a)$^{43}$Sc.

3 Claims, 1 Drawing Sheet

(56) References Cited

FOREIGN PATENT DOCUMENTS

| JP | 2009197024 A | 9/2009 |
|---|---|---|
| JP | 2009229201 A | 10/2009 |
| JP | 2012127659 A | 7/2012 |
| JP | 2013530384 A | 7/2013 |
| JP | 2013533459 A | 8/2013 |
| KR | 20060054329 A | 5/2006 |

OTHER PUBLICATIONS

Bommer J. et al.: "Study of 43Sc States with Proton Transfer Reactions on 42Ca"; Nuclear Physics; pp. 577-601; XP055206455; 1971; Amsterdam; Internet: URL:http://www.sciencedirect.com/science/article/pii/0375947471900996/pdf?md5=9754db367f45d30e89420bedcef5f559&pid=l-s2.0-0375947471900996-main.pdf.

McMurray W. et al.: "A Study of the Ca(p, n)SC Reactions (I). Energy levels in scandium isotopes"; Nuclear Physics A; pp. 6-16; 1967; XP055206549; DOI: 10.1016/0375-9474(67)90204-7; Internet: URL:http://www.sciencedirect.com/science/article/pii/0375947467902047/pdf?md5=f279c155318a0232251d344a990f12e9&pid=I-s2.0-0375947467902047-main.pdf.

Sadeghi M. et. al.: Nuclear data for the cyclotron production of 66GA, 86Y, 76Br, 64Cu and 43Sc in PET imaging§; Nukleonika; pp. 293-302; 2010; XP055206553; Internet: URL:http://www.nukleonika.pl/www/back/fulllvol55_2010/v55n3p293f.pdf.

Conlon T.W.: "Isomeric transitions in 43SC and 46V"; Physics Letters B; vol. 24; No. 13-14; pp. 661-662; 1967; XP055206573; ISSN: 0370-2693; DOI:10.1016/0370-2693(67)90373-5.

Plendl H.S. et al.: "Low-Lying energy levels in odd-mass Sc isotopes"; Nuclear Physics; vol. 73; No. 1; pp. 131-144; 1965; XP055206577; ISSN: 0029-5582, DOI:10.1016/0029-5582(65)90160-4.

Grandy T.B. et. al.: "The 42Ca (d, n) 432Sc reaction at Ed=5.15 MeV"; Nuclear Physics A; vol. 111, No. 2; pp. 469-480; 1968; XP055206608; ISSN 0375-9474, DOI: 10.1016/0375-9474(68)90139-5; pp. 469-470.

Foldzinska, A. et al., "Radiochemical Scheme for the Quantitative Isolation and Gamma-Spectometric Determination of La, Hf,and Sc in Neutron Activation Analysis of Refractory Materials" Journal of Radioanalytical Chemistry, vol. 21 (1974) pp. 507-517.

* cited by examiner

United States Patent US 10,357,578 B2

PRODUCTION OF 43SC RADIONUCLIDE AND RADIOPHARMACEUTICALS THEREOF FOR USE IN POSITRON EMISSION TOMOGRAPHY

BACKGROUND OF THE INVENTION

Field of the Invention

The present invention relates to a variety of methods for the production of the $^{43}$Sc radionuclide and radiopharmaceuticals thereof for use in Positron Emission Tomography.

Positron Emission Tomography (PET), in conjunction with other biomedical imaging methods like X-ray Computed Tomography (CT) or Magnetic Resonance Imaging (MRI), is one of the routinely-used diagnostic molecular imaging methods in nuclear medicine for the visualization of in vivo processes in cardiology, neurology, oncology or immunology.

The most widely-used radionuclide is $^{18}$F, having a half-life of 1.83 h, mostly in the form of 2-deoxy-2-($^{18}$F)fluoro-D-glucose (FDG). This is due to its nuclear decay properties and its availability, from a constantly growing number of biomedical cyclotrons. $^{18}$F-labeled compounds can be synthesized in large quantities in centralized GMP—(Good Manufacturing Practice) certified radiopharmacies and delivered over longer distances to hospitals operating PET centers. $^{18}$F is suitable to label small organic molecules, but has some disadvantages in labeling peptides or proteins.

Radiometals are more viable for these kinds of molecules. In recent years $^{68}$Ga, obtained from a $^{68}$Ge/$^{68}$Ga radionuclide generator system and having a half-life of 1.13 h, rose in prominence for PET in the form of a number of $^{68}$Ga-labeled compounds. Despite the numerous advantages of $^{68}$Ga-labeled compounds for PET diagnostics, there are a few relevant drawbacks. Firstly, the relatively short half-life requireseach site operating a PET scanner to also set up a radiopharmaceutical production facility, fulfilling all requirements imposed by legislation. Secondly, $^{68}$Ge/$^{68}$Ga-generators are able to provide a limited amount of radioactivity, for a maximum of about two to three patient doses per elution. Furthermore, it has been shown that $^{68}$Ga-labeled somatostatin analogues show different affinity profiles for human somatostatin receptor subtypes SSTR1-SSTR5, compared to their $^{177}$Lu and $^{90}$Y-labeled counterparts used for therapy. As a result, a correct therapy planning and dosimetry of patients, based on $^{68}$Ga PET imaging, appears questionable.

BRIEF SUMMARY OF THE INVENTION

To overcome these limitations, it is the objective of the present invention to provide a more appropriate alternative to $^{68}$Ga that would require the following properties: a positron-emitting radionuclide with a half-life of several hours; high positron yield but low positron energies (resulting in high PET resolution); a low number of accompanying low-energy gamma-rays (if any) with low intensities; and complex-chemical properties similar to $^{90}$Y or $^{177}$Lu (used for therapy) to allow its introduction in the diagnostic approach using existing clinically-relevant radiopharmaceuticals. Furthermore, its production should be attained in large activities at a biomedical cyclotron in a cost-effective manner and its chemical isolation accomplished in a short, relatively simple procedure, so that it can be directly used for subsequent labeling reactions.

This aim is achieved according to the present invention by a method for generating $^{43}$Sc, wherein one of the following methods is applied:
a) $^{43}$Ca(p,n)$^{43}$Sc, using enriched $^{43}$Ca at proton beam energies of 5 to 24 MeV;
b) $^{42}$Ca(d,n)$^{43}$Sc using enriched $^{42}$Ca and deuteron beam energies of 3 to 12 MeV, or
c) $^{46}$Ti(p,α)$^{43}$Sc using enriched $^{46}$Ti and proton beam energies of 10 to 24 MeV.

These three production paths are viable options to generate the $^{43}$Sc radionuclide to the desired extent in terms of volume and purity at a price that is competitive as compared to the aforementioned radionuclides, in particular $^{18}$F and $^{68}$Ga.

An advantageous method for the first option mentioned above can be achieved by the following production steps:
a) an enriched $^{43}$Ca target in the form of CaCO$_3$, Ca(NO$_3$)$_2$, CaF$_2$, or CaO powders or Ca metal having a content of $^{43}$Ca of 50% or higher is irradiated with a proton beam thereby turning the $^{43}$Ca content into $^{43}$Sc;
b) dissolving the irradiated enriched $^{43}$Ca target in acidic solution and passing the resulting solution through a first column loaded with DGA resin in order to absorb the $^{43}$Sc ions;
c) eluting the absorbed $^{43}$Sc ions by rinsing the first column with HCl into a second column loaded with a cation exchange resin, such as either DOWEX 50W-X2 or SCX cation exchange resin in order to sorb $^{43}$Sc in the second column; and
d) performing the elution of $^{43}$Sc from the second column using NH$_4$-acetate/HCl or NaCl/HCl.

An advantageous method for the second option mentioned above can be achieved by the following production steps:
a) an enriched $^{42}$Ca target in the form of CaCO$_3$, Ca(NO$_3$)$_2$, CaF$_2$ or CaO powders or Ca metal having a $^{42}$Ca content of 50% or higher is irradiated with a deuteron beam thereby turning the $^{42}$Ca content into $^{43}$Sc;
b) dissolving the irradiated enriched $^{42}$Ca target in HCl and passing the dissolved solution through a first column loaded with DGA resin in order absorb the $^{43}$Sc ions;
c) eluting the absorbed $^{43}$Sc ions by rinsing the first column with HCl into a second column loaded with a cation exchange resing, such as either DOWEX 50W-X2 or SCX cation exchange resin in order to sorb $^{43}$Sc in the second column; and
d) performing the elution of $^{43}$Sc from the second column using NH$_4$-acetate/HCl or NaCl/HCl.

In order to recycle the part of the $^{42}$Ca or $^{43}$Ca which has not been converted into $^{43}$Sc after the irradiation, the following steps can be applied:
a) an effluent from the first column comprising the valuable enriched Ca isotope in question, is evaporated to dryness in order to form a resultant residue;
b) the resultant residue is dissolved in deionized water and adjusted to a pH of 4.5-5 with ammonia solution and HCl, respectively, in order to form a solution comprising solved Ca(II) ions;
c) the solved content of Ca(II) is precipitated as Ca-oxalate by adding ammonium oxalate solution; and
d) filtering the precipitated Ca-oxalate and transferring the oxalate to the carbonate by slowly heating the filtered Ca-oxalate.

An advantageous method for the third option mentioned above can be achieved by the following production steps:
a) an enriched $^{46}$Ti target in form of titania powder is reduced to Ti metal wherein the titania powder having a content of $^{46}$Ti of 50% or higher, is irradiated with a proton beam thereby turning the $^{46}$Ti content into $^{43}$Sc;

b) the irradiated $^{46}$Ti target is dissolved in HCl; deionized water is added to dilute the solution to 3 to 5 M HCl;

c) the solution is passed through a first column comprising DGA resin wherein the first column is directly connected to a second column containing SCX cation exchange resin thereby sorbing the $^{43}$Sc on the SCX resin; and d) the sorbed $^{43}$Sc is eluted from the SCX column with SCX-Eluent (NaCl/HCl).

Correspondingly, a radiopharmaceutical to be applied in positron emission tomography comprises a radiometal-based radiopharmaceutical agent containing a bifunctional chelator such as a DOTA ligand (1,4,7,10-tetraazacyclodo-decane-1,4,7,10-tetraacetic acid) conjugated to a targeting vector (e.g. antibody, peptide, nanoparticle, vitamine and their derivates) and $^{43}$Sc being bound to the chelating agent. Preferably, this radiopharmaceutical comprises $^{43}$Sc to a radio content of 100 to 500 MBq, preferably about 200 MBq, for a dose for one positron emission tomography.

BRIEF DESCRIPTION OF THE SEVERAL VIEWS OF THE DRAWING

Preferred embodiments of the present invention are described hereinafter in more detail, in particular with reference to the following drawings which depict in.

DESCRIPTION OF THE INVENTION

Figure 1:
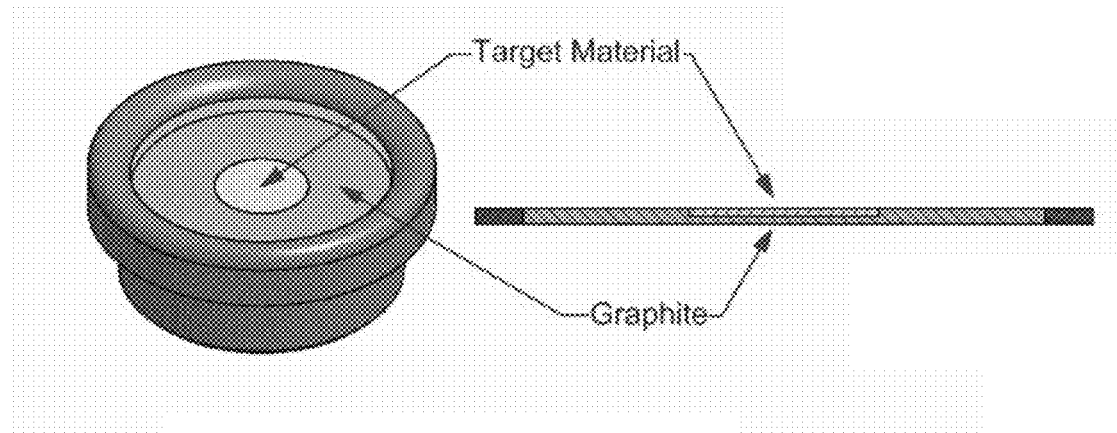
FIG. 1 schematically, a possible target design showing the position and relative thickness of the target material after pressing together with the graphite powder.

In search for such a longer-lived, positron-emitting radionuclide, the present invention identifies $^{43}$Sc as a more appropriate candidate than $^{68}$Ga, with chemical properties more similar to Y and the lanthanides and, thus, a more appropriate match than its Ga counterpart. The radioactive decay of $^{43}$Sc occurs with a low average positron energy of 0.476 MeV ($^{68}$Ga: 0.830 MeV), a high total positron yield of 88.1% ($^{68}$Ga: 88.9%), and an ideal half-life of 3.89 h ($^{68}$Ga: 1.13 h), thereby, allowing its transport over long distances to the costumer (i.e. >500 km). Its decay is associated with a relatively low energy gamma-ray of 373 keV and 23% abundance ($^{68}$Ga: 1077 keV, 3.2%), which will not influence PET imaging negatively, as modern PET scanners can be operated using a relatively narrow energy window (i.e. 440-665 keV). As a result, this radionuclide has the potential to overcome the abovementioned limitations of $^{68}$Ga, while offering superior properties. Scandium is known to form complexes with very high stability constants with DOTA (1,4,7,10-tetraazacyclododecane-1,4,7,10-tetraacetic acid), a widely-used chelator for radiometals in radiopharmaceutical chemistry. The stability constants are comparable to lutetium or yttrium as they all form complexes with square-antiprismatic geometry, whereas they are lower for gallium with distorted octahedron geometry. $^{68}$Ga can, therefore, easily be exchanged with $^{43}$Sc in radiopharmaceuticals employing the DOTA chelator and can be introduced directly into a GMP-compliant cassette labelling system, such as one provided by Eckert & Ziegler for the labelling of DOTA-ligands in the form of DOTA-TATE, DOTA-TOC, DOTA-BASS, DOTA-PSMA, DOTA-Folate etc.

The present invention also describes a variety of methods for the production of $^{43}$Sc, in sufficient quantities and high radionuclidic purity, by means of a biomedical cyclotron, i.e. with proton beams in the energy range of 10-24 MeV (or deuteron beams in the energy range of 3 to 12 MeV).

The present invention also describes the required radiochemical procedures to extract $^{43}$Sc from its target material in quality and quantity suitable for direct labeling reactions and for future medical application. In addition, procedures to recover the valuable, enriched target materials are disclosed.

Current Status of Research in the Field

Radiopharmaceuticals comprising metallic radionuclides are gaining in importance in diagnostic and therapeutic nuclear medicine. A prime example is $^{99m}$Tc, which is currently the most widespread metallic diagnostic radionuclide in nuclear medicine and recently gained attention due to a worldwide supply crisis. The search for alternative procedures is of utmost importance. Examples of therapeutic metallic radionuclides are $^{90}$Y used in Zevalin® (Ibritumomab tiuxetan labeled with $^{90}$Y), $^{177}$Lu in Lutathera® also known as $^{177}$Lu-DOTA-TATE ($^{177}$Lu-DOTA$^0$-Tyr$^3$-Octreotate; $^{177}$Lu-DOTA-DPhe-c(Cys-Tyr-DTrp-Lys-Thr-Cys)-Thr; DOTA: 1,4,7,10-tetraazacyclododecane-1,4,7,10-tetraacetic acid), or even $^{223}$Ra ($^{223}$RaCl$_2$) in Xofigo® for the treatment of patients with prostate cancer and bone metastases.

In recent years, somatostatin-receptor-targeted radionuclide therapy of neuroendocrine tumors (NET) has gained much attention. Therapies using $^{90}$Y and $^{177}$Lu have proven so successful that the International Atomic Energy Agency (IAEA), in cooperation with EANM and SNMMI, has recently issued a practical guidance on peptide receptor radionuclide therapy (PRRNT) for NET. PRRNT was first administered in 1996 in Basel, Switzerland. Other therapies targeting G-protein coupled receptors with peptides, the folate receptor or using monoclonal antibodies conjugated to suitable metallic radionuclides are currently in pre-clinical and clinical trials or are already licensed as radiopharmaceuticals. Quite often, these pharmaceuticals can also be labeled with a relatively short-lived diagnostic radionuclide, especially if the pharmacokinetics is fast. Central to research efforts are isotopes of elements that offer ideal radionuclidic pairs for diagnostic and therapeutic purposes (theranostics or theragnostics). In this way, the same pharmaceutical entity could be labeled with either a diagnostic or a therapeutic nuclide and, due to negligible isotopic effects, one can assume that the therapeutic effect will take place in the positions previously identified by imaging. There is hope that such an approach will facilitate the correct therapy planning and dosimetry of patients, a problem which has not effectively been solved to date.

An inspection of the chart of nuclides reveals that very few such "matched pairs" exist, especially if one requirement is that the diagnostic radionuclide must be suitable for PET. No suitable matched positron emitter exists for the two most widely-employed therapeutic radionuclides in PRRNT, $^{90}$Y and $^{177}$Lu ($^{86}$Y with a low positron branch of 31.9% and numerous high-intensity, high-energy gamma-rays cannot be considered as particularly suitable without the application of correction methods and also concerning radiation dose to patients and personnel, but has been used in patients nonetheless).

Therefore, radionuclides that behave similarly chemically, resulting in comparable biological behavior, should be taken into consideration. Recently, the diagnosis of NET was successfully performed using $^{68}$Ga-radiolabeled derivatives of octreotide. $^{68}$Ga is obtained from a $^{68}$Ge/$^{68}$Ga radionuclide generator system and has a half-life of 1.13 h. While diagnostic results are far superior to Single-Photon Emission Computed Tomography (SPECT) of $^{111}$In-radiolabeled derivatives, there are drawbacks to using $^{68}$Ga. The relatively short half-life requires each site operating a PET scanner to also set up a radiopharmaceutical production site, fulfilling all new requirements imposed by legislation related to GMP. Furthermore, current $^{68}$Ge/$^{68}$Ga radionuclide generator systems are limited to about 2 GBq of activity, which results in the production of not more than two to three patient doses per generator elution. The half-life of $^{68}$Ge (270.82 d) requires an annual replacement of the generator, at best. The current system makes $^{68}$Ga-labeled radiopharmaceuticals and its required infrastructure labor-intensive and, thus, is seen as an expensive application, as experienced by the applicants' recent introduction of $^{68}$Ga-DOTA-TATE.

Compared to e.g. $^{18}$F-labeled compounds that can be synthesized in GMP-certified radiopharmacies and delivered to hospitals operating PET centers over further distances, the abovementioned drawbacks of $^{68}$Ga may limit the widespread application of this radionuclide for PET imaging. Furthermore, it has been shown that $^{68}$Ga-labeled somatostatin analogues show different affinity profiles for human somatostatin receptor subtypes SST1-SST5, compared to their $^{177}$Lu and $^{90}$Y counterparts used for therapy. As a result, a correct therapy planning and dosimetry of patients based on $^{68}$Ga imaging appears questionable.

Taking the abovementioned statements into account, $^{44}$Sc-radiolabeled radiopharmaceuticals were considered as an alternative, especially since the chemical behavior of Sc is expected to be more similar to Y and Lu than its Ga counterpart. This radionuclide, with an attractive half-life of 3.92 h, can be obtained from a $^{44}$Ti/$^{44}$Sc radionuclide generator system, or be produced at a 10-20 MeV biomedical cyclotron via the $^{44}$Ca(p,n)$^{44}$Sc nuclear reaction, producing a much greater yield than extracting it from a generator.

The only serious drawback of $^{44}$Sc as positron-emitting radionuclide is the co-emission of an 1157 keV gamma-ray with 99.9% intensity. Compton scattered gamma-rays can interfere with the correct reconstruction of the location of the annihilation reaction of the positron and, thus, impair the obtained PET image. The high-energy gamma-ray also adds to the radiation exposure of patients and personnel. Nevertheless, it should be mentioned that the co-emitted 1157 keV gamma-ray of $^{44}$Sc was used for "3γ imaging" using detection of $\beta^+\gamma$ coincidences with liquid xenon as detection medium. The first human patient was diagnosed by administrating 37 MBq of $^{44}$Sc-DOTA-TOC ($^{44}$Sc-DOTA$^0$)-Tyr$^3$-octreotide; $^{44}$Sc-DOTA-DPhe-c(Cys-Tyr-DTrp-Lys-Thr-Cys)-Thr(ol)). High-quality PET/CT images were recorded even 18 h post injection (p.i.), demonstrating that the uptake kinetics can be followed over a relatively long period compared to the $^{68}$Ga-labeled analogue and that an individual dosimetry of a subsequent therapeutic application with a longer-lived $^{90}$Y- or $^{177}$Lu-analogue may be possible.

The biomedical cyclotrons used mainly for $^{18}$F production are designed to accelerate protons and, quite often, also deuterons. According to the present invention, three nuclear reactions using a biomedical cyclotron are used to produce clinically-relevant activities of $^{43}$Sc. The reactions proposed are:

a) $^{43}$Ca(p,n)$^{43}$Sc, using commercially available, enriched $^{43}$Ca (natural abundance 0.153%) at proton beam energies of 5 to 24 MeV;
b) $^{42}$Ca(d,n)$^{43}$Sc, using commercially available, enriched $^{42}$Ca (natural abundance 0.647%) and deuteron beam energies of 3 to 12 MeV, or
c) $^{46}$Ti(p,α)$^{43}$Sc, using commercially available, enriched $^{46}$Ti (natural abundance 8.25%) and proton beam energies of 10-24 MeV.

Due to the relatively low beam energies, the production of $^{43}$Sc can be established at most biomedical cyclotrons equipped with a solid target station, resulting in an overall cost reduction due to centralized production. Due to its longer half-life, $^{43}$Sc-radiopharmaceuticals can be produced concurrently or ahead of $^{18}$F-labeled ones and shipped together to the customer.

The present disclosure describes the $^{43}$Sc production using different production routes and establishes the most appropriate one such that the product can be used for the labeling of compounds for clinical evaluation. Different $^{43}$Sc-labeled DOTA-peptides, based on ligands binding mainly to SSTR2, are compared to the $^{177}$Lu, $^{90}$Y, and $^{68}$Ga-labeled counterparts with respect to binding affinity, internalization, stability and in vivo properties.

$^{43}$Sc can be produced at a biomedical cyclotron using three different production routes, which will be discussed in more detail. Its production using an α-particle beam in the reaction $^{40}$Ca(α,n)$^{43}$Ti→$\beta^+$→$^{43}$Sc is an option, however, accelerators which are able to deliver α-particle beams are scarce and more expensive to operate. Furthermore, the active target thickness is much more limited with α-particle beams significantly reducing the overall production yield.

As a result, the $^{43}$Ca(p,n)$^{43}$Sc, $^{42}$Ca(d,n)$^{43}$Sc, or $^{46}$Ti(p,α)$^{43}$Sc reactions are considered. The TENDL-2013 calculations, a TALYS-based evaluated nuclear data library, were used to estimate the activity and the radionuclidic purity that could be obtained by irradiation of commercially-available enriched target materials. Where available, the predicted TENDL-2013 calculations were compared with experimentally-determined production reaction cross sections. It was assumed that 10 mg/cm$^2$ of the enriched target element were irradiated at a beam energy corresponding to the maximum of the predicted excitation function over two hours and an intensity of 25 μA. After the irradiation, an one-hour waiting period is considered before chemical processing and a processing time of one hour including the labeling of a pharmaceutical. Assuming an 85% chemical yield of the Sc/Ca separation and an 85% yield of the labeling procedure, the theoretical product yields listed in Table 1 can be expected under the aforementioned conditions. These yields were based on the following isotopic compositions of commercially available, enriched target materials:

$^{43}$Ca-Target:
$^{40}$Ca (28.50%), $^{42}$Ca (1.05%), $^{43}$Ca (57.9%), $^{44}$Ca (12.36%), $^{46}$Ca (<0.003%), $^{48}$Ca (0.19%)

$^{42}$Ca-Target:
$^{40}$Ca(17.79%), 42Ca (80.80%), $^{43}$Ca (0.39%), $^{44}$Ca (0.97%), $^{46}$Ca (<0.01%), (<0.05%)

$^{46}$Ti-Target:
$^{46}$Ti(96.9%), $^{47}$Ti (0.45%), $^{48}$Ti (2.32%), $^{49}$Ti(0.17%), $^{50}$Ti (0.16%)

TABLE 1

Calculated yields and radionuclidic purity of three different reactions to produce $^{43}Sc$

| Nuclear reaction | price[1] CHF/dose | Beam energy on target (MeV) | $^{43}Sc$ 3.89 h (Bq) | $^{44g}Sc$ 3.97 h (Bq) | $^{44m}Sc$ 2.44 d (Bq) | $^{46g}Sc$ 83.79 d (Bq) | $^{47}Sc$ 3.35 d (Bq) | $^{48}Sc$ 1.82 d (Bq) | $^{49}Sc$ 57.2 m (Bq) | radionuclidic purity (% Sc activity) $^{43}Sc$ (%) | $^{43}Sc+^{44g}Sc$ (%) |
|---|---|---|---|---|---|---|---|---|---|---|---|
| $^{43}Ca(p,n)^{43}Sc$ | 19.90 | 9 | $1.9 \times 10^9$ | $5.9 \times 10^8$ | $2.9 \times 10^6$ | $<3.9 \times 10^2$ | $1.0 \times 10^4$ | $2.0 \times 10^5$ | | >76.26 | >99.87 |
| $^{42}Ca(d,n)^{43}Sc$ | 10.80 | 5 | $2.0 \times 10^9$ | $1.0 \times 10^7$ | $3.0 \times 10^5$ | $<6.9 \times 10^1$ | $<4.3 \times 10^4$ | $<2.1 \times 10^5$ | $<1.3 \times 10^6$ | >99.40 | >99.91 |
| $^{46}Ti(p,\alpha)^{43}Sc$ | 24.80 | 16 | $2.2 \times 10^8$ | $2.3 \times 10^6$ | $5.4 \times 10^4$ | $7.9 \times 10^2$ | $1.4 \times 10^4$ | | | 98.97 | 99.97 |

[1]Price of the enriched target material for 1 patient dose (200 MBq), assuming a target recovery yield of 80%.

The $^{43}Ca(p,n)^{43}Sc$ Nuclear Reaction:

The calculated maximum of the excitation reaction corresponds to about 388 mb ($10^{-27}$ cm$^2$) at a beam energy of 9 MeV. The calculated cross sections are in reasonable agreement with experimental data and the applicants' own measurements. As can be seen from Table 1, the yield of 2 GBq $^{43}Sc$ is good, however, co-production of $^{44g}Sc$ is significant. Considering the fact that $^{44g}Sc$ has an almost identical half-life and was discussed as a suitable PET nuclide, all other Sc nuclides contribute <0.12% of the total Sc activity, with the long-lived $^{46g}Sc$ comprising only <2.1× $10^{-5}$% of the total activity.

The $^{42}Ca(d,n)^{43}Sc$ Nuclear Reaction:

The calculated maximum of the excitation reaction corresponds to about 280 mb ($10^{-27}$ cm$^2$) at a beam energy of 5 MeV. The yield of 2 GBq of $^{43}Sc$ is good and the co-production of $^{44g}Sc$ is <1%. In relation to $^{43}Sc+^{44g}Sc$, all other Sc radionuclides contribute <0.11% of the total Sc activity, the largest contributor being $^{49}Sc$ with a half-life of only 57.2 m. The long-lived $^{46g}Sc$ comprises only <3.5×10$^{-6}$% of the total activity. In maximum production cross sections of only about 80 mb ($10^{-27}$ cm$^2$) have been reported. Own measurements indicate production cross sections in the range of 125 to 225 mb ($10^{-27}$ cm$^2$) for beam energies between 3.6 and 7.8 MeV.

The $^{46}Ti(p,\alpha)^{43}Sc$ Nuclear Reaction:

The calculated maximum of the excitation reaction corresponds to about 31 mb ($10^{-27}$ cm$^2$) at a beam energy of 16 MeV. The available experimental reaction cross section data is about 40 mb at 16 MeV (renormalized to 100% $^{46}Ti$ isotopic abundance) and, thus, in reasonable agreement. The yield of 0.2 GBq of $^{43}Sc$ is lower by one order of magnitude compared to the other two production reactions but the co-production of $^{44g}Sc$ is <1%. In relation to $^{43}Sc+^{44g}Sc$, all other Sc radionuclides contribute <0.02% of the total Sc activity. The long-lived $^{46g}Sc$ comprises only 3.6×10$^{-4}$% of the total activity.

A chemical procedure was established for all three nuclear reactions that quantitatively recovers the enriched target materials. Assuming a conservative recovery yield of 80%, the material costs per patient dose (200 MBq $^{43}Sc$) are given in Table 1. The current cost of the target materials is as follows: $^{43}Ca$ 94.50 CHF/mg, $^{42}Ca$ 54.00 CHF/mg, and $^{46}Ti$ 13.65 CHF/mg. For comparison, the cost of $^{68}Ga$ was calculated at 85 CHF/dose, assuming that a generator can be eluted 200 times before breakthrough of $^{68}Ge$ starts to occur. The abovementioned considerations are provided to demonstrate that the production costs of $^{43}Sc$ are insignificant compared to the costs of the radiopharmaceutical product, especially taking into account that biomedical cyclotrons are usually only in operation for few hours per day to produce $^{18}F$.

Taking the yield of $^{43}Sc$ and the co-production of $^{46g}Sc$ as long-lived contaminant into consideration, the $^{42}Ca(d,n)$ $^{43}Sc$ reaction appears, currently, to be most favorable. The $^{46}Ti(p,\alpha)^{43}Sc$ reaction also delivers a relatively pure product. For this reason, a careful experimental assessment of the cross section was necessary. The $^{43}Ca(p,n)^{43}Sc$ reaction remains viable, especially if more highly-enriched $^{43}Ca$ becomes available. It is, therefore, essential to investigate the product spectrum of all three reactions experimentally and to optimize the production of $^{43}Sc$ in relation to the long-lived $^{46g}Sc$ by optimization of the beam energy.

Targets are prepared by pressing either enriched $^{42}Ca$ or $^{43}Ca$ in the form of the metal or in the form of Ca compounds such as $CaCO_3$, $Ca(NO_3)_2$, $CaF_2$ or $CaO$ powders or Ca metal into the groove of the target holder. The target holder provides a volume of up to 0.28 cm$^3$ accommodating up to 100 mg of the enriched isotope in question. In the case of Ti targets, the enriched material can only be purchased in the form of $TiO_2$. The rapid dissolution of $TiO_2$ in a hot-cell environment presents serious difficulties, if hot sulfuric acid or concentrated HF were to be avoided. As a result, the enriched Ti target material is first quantitatively reduced to Ti metal. As can be seen from Table 1, the use of about 100 mg enriched $^{46}Ti$ will result in the production of >10 patient doses per irradiation, thus, making the $^{46}Ti(p,\alpha)$ reaction a viable option, despite the low production cross section.

A chemical strategy to isolate $^{43}Sc$ from irradiated target materials in quantity and quality sufficient for radiopharmaceutical applications is provided, including the recovery of the valuable target material in question. The product must be in a chemical form that is directly usable for a subsequent labeling process.

The chemical strategy for the production of $^{43}Sc$ from enriched Ca target material will be similar to the one established for $^{44}Sc$.

Design, Manufacturing and Irradiation of Enriched $^{42}CaCO_3$ or $^{43}CaCO_3$ Targets:

To manufacture the targets, 10±1 mg enriched $^{42}CaCO_3$ or $^{43}CaCO_3$ powder is placed on top of ~160 mg graphite powder (99.9999%) and pressed with 10 t of pressure. The targets have dimensions of 0.4-0.5 mm thickness and a diameter of 16 mm (the pressed $^{42}CaCO_3$ or $^{43}CaCO_3$ powder have a calculated depth of 190 μm and diameter of 6 mm in the center of the disc). The encapsulated $^{42}CaCO_3$ or $^{43}CaCO_3$ pressed target is placed in a target holder system before introduction into the irradiation facility (see FIG. 1). The thickness of the target is driven by the high cost of the enriched material and, therefore, can be increased for production runs.

FIG. 1 indicates a possible target design showing the position and relative thickness of the target material after pressing together with the graphite powder. The target material is covered by an aluminum lid in the bombardment configuration.

Preparation of Resin Columns:

A column (1 mL cartridge fitted with 20 μm frit, cut to a length of 27 mm) is filled with ~70 mg of DGA resin (Triskem International, France) and a 20 μm frit placed on top of the resin. The DGA column is preconditioned with 3 M HCl. A second column is used to concentrate the $^{43}$Sc. Two methods can be followed for the concentration of product. Method A: The second column (1 mL cartridge fitted with 20 μm frit) was filled with ~140 μL of DOWEX 50W-X2 and a 20 μm frit placed on top of the resin. The column is preconditioned with 0.1 M HCl solution. Method B:

Alternatively, SCX (Agilent Technologies Inc., USA) cartridges are used for the concentration step, which can be used as purchased without preconditioning.

Figure 2:
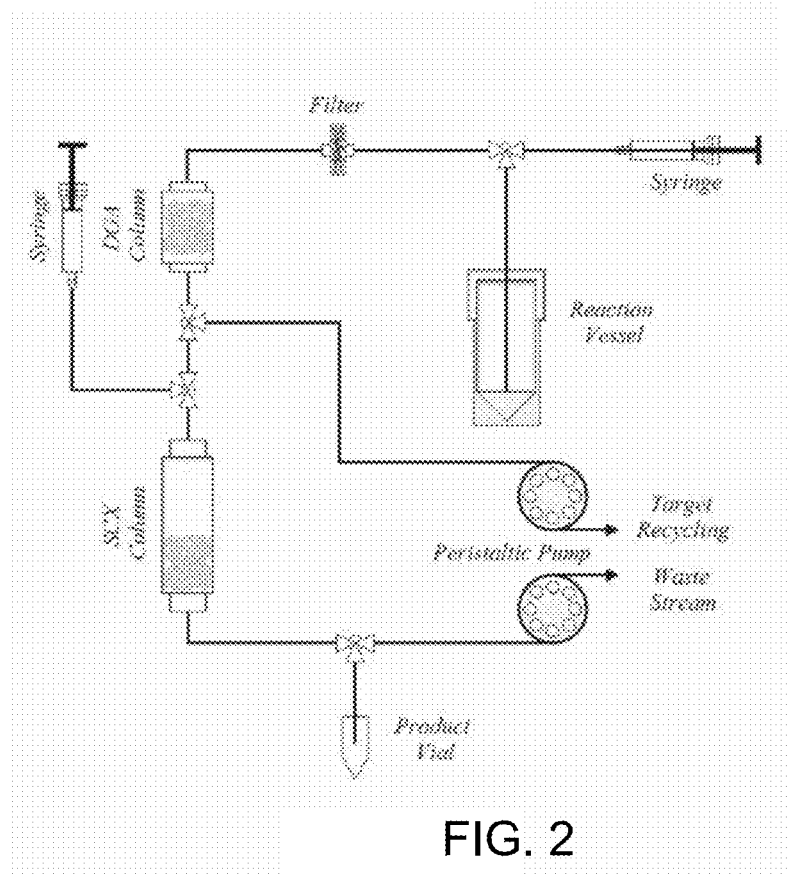
FIG. 2 a schematic diagram of the $^{43}$Sc production panel using enriched Ca.

Separation of $^{43}$Sc from Calcium Target Material:

The activated target is removed from its aluminum encapsulation and transferred into a glass vial (reaction vessel), dissolved in 2.5 mL 3 M HCl and loaded onto the DGA column, being passed over a 10 mm long filter (1 mL cartridge fitted with a 20 μm frit) beforehand. The target container is rinsed with 2.5 mL 3 M HCl and the solution passed over the DGA resin. A further 4 mL 3 M HCl is applied directly onto the DGA column to ensure complete removal of residual Ca(II). A system of syringes and three-way valves are used to transfer solutions from outside into the hot cell (FIG. 2). The first column is directly connected to the second column and the $^{43}$Sc eluted from the DGA resin with 4 mL 0.1 M HCl. The solution is sorbed on the second column containing either DOWEX 50W-X2 (Method A) or SCX (Method B) cation exchange resin. The elution of $^{43}$Sc is performed via a separate valve (FIG. 2) using 1.5 mL 0.75 M NH$_4$-acetate/0.2 M HCl (pH 4.5-5.0) for Method A and 0.7 mL 5 M NaCl/0.13 M HCl (pH 0-0.5) for Method B, respectively. In order to collect $^{43}$Sc in a suitably small volume the acetate/HCl eluate (Method A) is fractionized into three Eppendorf vials, each containing ~500 μL. The activity of the eluted fractions is monitored with a radioactivity sensor. Fractionized collection is not necessary in the case of Method B. The chemical yield of Sc is >98%.

FIG. 2 shows a schematic diagram of the $^{43}$Sc production panel (Method B) using enriched Ca.

Enriched $^{42}$CaCO$_3$ or $^{43}$CaCO$_3$ target material recycling: The effluent from the DGA column of several production runs, containing the valuable enriched Ca isotope in question, is evaporated to dryness. The resultant white residue is dissolved in 20 mL deionized water and adjusted to a pH of 4.5-5 with 2.5% ammonia solution and 1 M HCl, respectively. Ca(II) is precipitated as Ca-oxalate by adding 20 mL 0.3 M ammonium oxalate solution. The mixture is left to stand for 2 hours to ensure complete precipitation, filtered through a porcelain filter crucible (8 μm pore size) and the oxalate transferred to the carbonate by slowly heating to 500° C. Thus, the valuable enriched materials are again available to manufacture targets. A preceding ICP-OES analysis indicated a Ca concentration of 450 ppm, with minor metallic contaminants (2 ppm Al and 1 ppm Sr). An overall recovery yield of 98% was obtained with the ammonium oxalate precipitation method. The recovered target material provided $^{43}$Sc of the same quality as was obtained with targets from the originally-purchased $^{43}$CaCO$_3$.

The production of $^{43}$Sc using the $^{46}$Ti(p,α)$^{43}$Sc reaction requires a separation of Sc from Ti and a recycling step for the enriched $^{46}$Ti target material. The chemical separation strategy is based on literature data and ongoing research and development at PSI. With the development of a $^{44}$Ti/$^{44g}$Sc generator system, the chemical separation of Ti and Sc has already been the subject of some research efforts.

The chemical separation of Ti and Sc has proven to be difficult, as Ti is easily oxidized and its oxide is only effectively dissolved using hot, concentrated sulfuric acid. A further headache is the fact that extensive heat is required to evaporate the sulfuric acid, as it boils at over 300° C. More recent attempts at separating these two elements involved the use of hydrofluoric acid (HF). HF was used to dissolve the target material, before it was diluted and loaded on an anion exchange resin column. With Ti retained, the eluted Sc (dilute HF and dilute nitric acid) is loaded on to a cation exchange resin and eluted with dilute ammonium acetate. Another system, which involved the separation of $^{44}$Ti from Sc target material, saw a concentrated solution of hydrochloric acid being used to pass through an anion exchange resin, allowing the Ti to be retained and the Sc to pass though.

A chemical strategy to isolate $^{43}$Sc produced in the $^{46}$Ti(p,α) reaction from irradiated Ti target materials in quantity and quality sufficient for radiopharmaceutical applications is provided, including the recovery of the valuable target material in question. The product must be in a chemical form directly usable for a subsequent labeling process.

Reduction of $^{46}$TiO$_2$:

Up to 250 mg $^{46}$TiO$_2$ are mixed with 40% surplus CaH$_2$, metals basis in an oxygen-free Ar-environment. A tablet is pressed with 5 t pressure for 2 minutes and in a molybdenum crucible inserted into an Ar-flooded oven. The oven is heated up to 900° C. in about 30 minutes, and the temperature is kept at 900° C. for 1 hour. The oven is cooled down to 100° C., which takes about 2-3 hours. The reduction is complete when the white TiO$_2$ transformed into black Ti. The tablet is placed on a Millipore-Filter (0.45 μm) in a Buchner funnel and washed with about 20 ml deionized water, whereby the tablet disintegrates. The CaO is dissolved by washing with 100-150 mL acetic acid, suprapur (1:4) over a time period of 3 hours. The filter is rinsed with deionized water until the effluent of the Buchner funnel is pH neutral. The resulting Ti-powder is dried in a desiccator overnight.

Design, Manufacturing and Irradiation of Enriched $^{46}$Ti Metal Targets:

The manufacturing of $^{46}$Ti metal targets proceeds analogous to the preparation of enriched CaCO$_3$-targets. To manufacture the targets, 10±1 mg enriched $^{46}$Ti metal powder is placed on top of ~160 mg graphite powder (99.9999%) and pressed with 10 t of pressure. The resulting tablet is encapsulated in aluminum and placed in a target holder system.

Preparation of Resin Columns:

A column (1 mL cartridge fitted with 20 μm frit, cut to a length of 27 mm) is filled with ~70 mg of DGA resin (TrisKem International, France) and a 20 μm frit placed on top of the resin. The DGA column is cleaned and preconditioned with 4 mL 6 M HCl and 9 mL 4 M HCl.

Separation of $^{43}$Sc from Titanium Target Material:

The irradiated $^{46}$Ti-graphite target is dissolved in 5 mL 6 M HCl at 180° C. for 10 minutes, 2 mL deionized water is added to dilute the solution to 4 M HCl.

The starting solution is passed through the DGA resin column. The vial is flushed with 3 mL 4 M HCl, passed through the resin column, with any remaining impurities removed from the DGA column with an additional 8 mL 4M HCl. The DGA column is directly connected to a second column containing SCX cation exchange resin. $^{43}$Sc is eluted from the DGA column with 10 mL 0.05 M HCl and sorbed on the SCX column. Elution of the product from the SCX column with 700 µL SCX-Eluent (4.8M NaCl/0.1M HCl) yields $^{43}$Sc directly available for labelling reactions. The chemical yield of Sc is >98%.

Labelling Reactions:

The product is placed into a Reactivial containing 2 mL 2M sodium acetate buffer and 10 µg peptide (DOTA-chelator). The resultant solution is heated at 100° C. for 10 minutes, after which it is passed through a Sep-Pak C18 Lite cartridge (Waters Corporation, USA). The cartridge is rinsed with 2 mL 0.9% saline, before the product is eluted with 2 mL 50% ethanol. The addition of gentisic acid ensures that no radiolysis of the labelled product occurs.

The applicants believe that $^{43}$Sc represents a highly promising radionuclide with unique and important scientific, clinical and industrial implications.

The invention claimed is:

1. A method for generating $^{43}$Sc, which comprises:
    performing a nuclear reaction of $^{42}$Ca(d,n)$^{43}$Sc using enriched $^{42}$Ca and deuteron beam energies of 3 to 12 Mev.

2. The method according to claim 1, which further comprises:
    irradiating the enriched $^{42}$Ca target in form of CaCo$_3$, Ca(NO$_3$)$_2$, CaF$_2$, or CaO powders or Ca metal having a $^{42}$Ca content of 50% or higher with \hte deuteron beam thereby turning $^{42}$Ca content into the $^{43}$Sc;
    dissolving irradiated enriched $^{42}$Ca target in acidic solution and passing a resulting solution through a first column loaded with DGA resin in order to absorb $^{43}$Sc ions;
    eluting absorbed $^{43}$Sc ions by rinsing the first column with HCl into a second column loaded with a cation exchange resin in order to sorb $^{43}$Sc in the second column; and
    performing an elution of the $^{43}$Sc from the second column using NH$_4$-acetate/HCl or NaCl/HCl.

3. The method according to claim 1, which further comprises:
    evaporating an effluent from the first column containing an enriched Ca isotope to dryness in order to form a resultant white residue;
    dissolving the resultant white residue in deionized water and adjusted to a pH of 4.5-5 with ammonia solution and HCl, respectively, in order to form a solution containing solved Ca(II) ions;
    precipitating a solved content of Ca(II) as Ca-oxalate by adding ammonium oxalate solution; and
    filtering precipitated Ca-oxalate and transferring an oxalate to a carbonate by slowly heating filtered Ca-oxalate.

* * * * *